Figure 1:
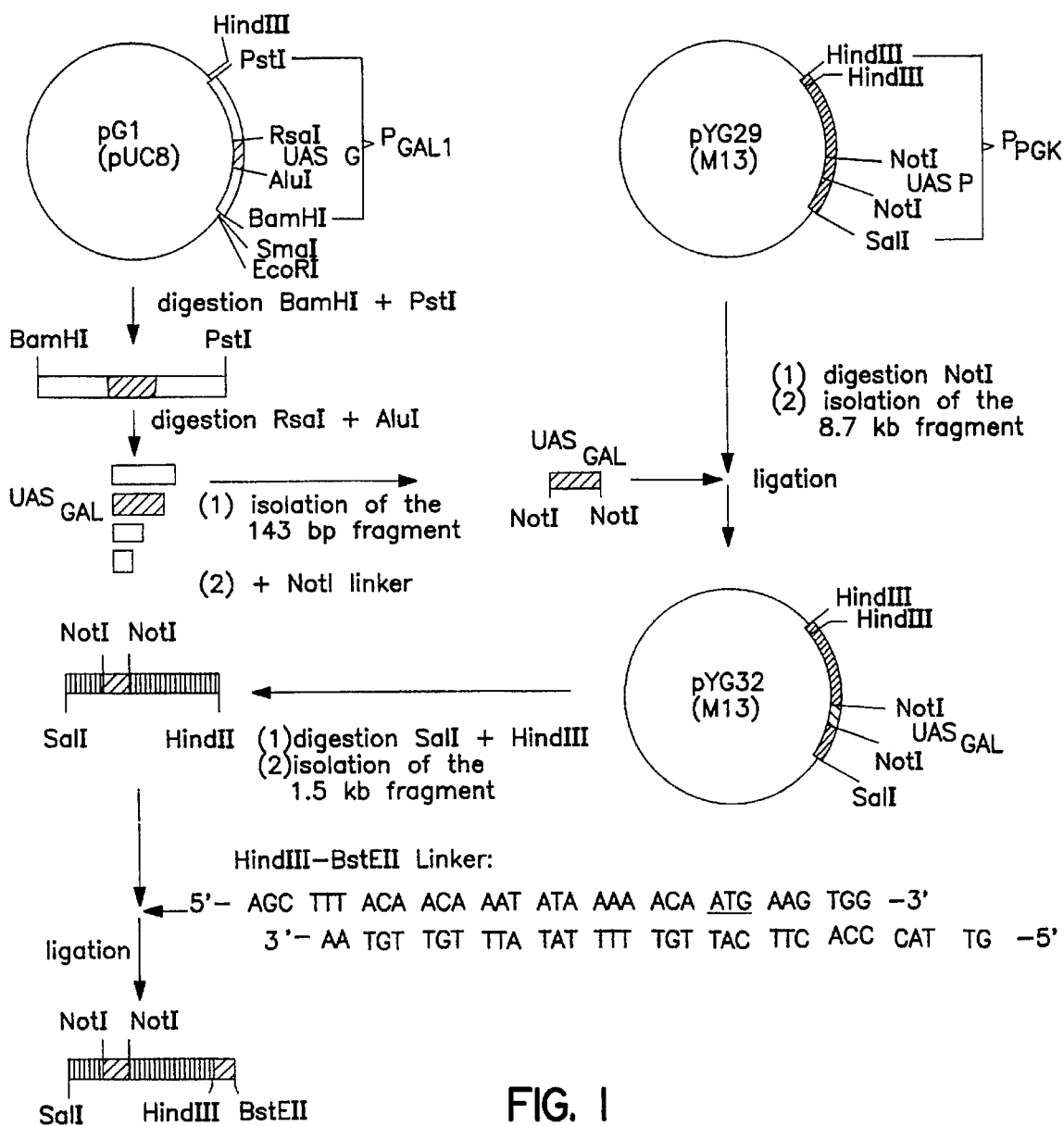

United States Patent [19]
Fleer et al.

[11] Patent Number: 5,633,146
[45] Date of Patent: May 27, 1997

[54] METHOD FOR PRODUCING RECOMBINANT PROTEINS AND HOST CELLS USED THEREIN

[75] Inventors: Reinhard Fleer, Bures sur Yvette; Alain Fournier, Chatenay Malabry; Patrice Yeh, Paris, all of France

[73] Assignee: Rhone-Poulenc Rorer S.A., Antony, France

[21] Appl. No.: 454,778

[22] Filed: May 31, 1995

Related U.S. Application Data

[63] Continuation of Ser. No. 175,417, Jun. 30, 1992, abandoned.

[30] Foreign Application Priority Data

Jul. 2, 1991 [FR] France ................... 91 08217

[51] Int. Cl.$^6$ .................... C12N 1/106; C12N 1/19; C12N 15/63; C12N 15/81
[52] U.S. Cl. .................... 435/69.1; 435/254.11; 435/69.3; 435/69.4; 435/69.5; 435/69.51; 435/69.52; 435/69.6; 435/69.7; 435/69.8; 435/69.9; 435/71.1; 435/189; 435/192; 435/198; 435/201; 435/226; 435/227; 435/254.2; 435/255.1; 435/911
[58] Field of Search .................... 435/254.11, 69.1, 435/69.3, 69.4, 69.5, 69.51, 69.52, 69.6, 69.7, 69.8, 69.9, 71.1, 189, 192, 198, 201, 226, 227, 254.2, 255.1, 911

[56] References Cited

PUBLICATIONS

Bio/Technology 8:135–9, 1990, van den Berg, van der Laken, van Ooyen, Renniers, Rietveld et al., Kluyveromyces as a Host for Heterologous Gene Expression: Expression and Secretion of Prochymosin, English Original.

J. Cell. Biochem. Suppl. 14C:68, Abst. H402, 1990, Yeh, Fleer, Chen, Maury, Faulconnier et al., pKD1–Based Secretion Vectors for the Production of Human Recombinant Proteins in Kluyveromyces Yeasts, English Original.

Yeast 6 (Special Issue):S449, 1990, Fleer, Yeh, Becquart, Amellal, Maury et al., pKD1–Based Multi–Copy Vectors Mediate High Level Secretion of Human Serum Albumin (HSA) from . . . , English Original.

WO83/04050 May 19, 1983, Hollenberg, Das, De Leeuw, van den Berg, Cloning System for Kluyveromyces Species, English Original.

EP0096910 May 19, 1983 Edens, Ledeboer, Verrips, Van Den Berg, Yeast of the genus kluyveromyces modified for the expression of preprothaumatin or its various . . . English Original.

EP0241435 Mar. 25, 1987 Falcone, Fukuhara, Frontali, Vectors for the cloning and expression of heterologous genes in yeast and the yeast strains transformed by said . . . English Original.

EP0301670 Jul. 28, 1988 van den Berg, van Ooyen, Rietveld, Kluyveromyces as a host strain, English Original.

EP0361991, Aug. 4, 1989, Fleer, Fukuhara, Yeh, Method for the microbiological preparation of human serum albumin and other heterologous proteins, English Original.

Primary Examiner—Robert A. Wax
Assistant Examiner—Rebecca Prouty
Attorney, Agent, or Firm—Julie K. Smith; Martin F. Savitzky

[57] ABSTRACT

Novel genetically engineered yeast strains of genus *Kluyveromyces lactis*, their preparation, and the use thereof for producing recombinant proteins, are described.

19 Claims, 6 Drawing Sheets

METHOD FOR PRODUCING RECOMBINANT PROTEINS AND HOST CELLS USED THEREIN

This is a continuation of application Ser. No. 08/175,417 filed Jun. 30, 1992, now abandoned.

The present invention relates to new yeast strains modified by genetic engineering, their preparation and their use for the production of recombinant proteins. More particularly, the invention relates to new yeast strains of the genus Kluyveromyces.

There is a large selection of host organisms, such as mammalian cells or microorganisms, which may potentially be used with a view to the production of recombinant proteins.

The use of mammilian cells modified by recombinant DNA techniques has the advantage of leading to products very close to those of natural origin. However, the culture of these cells is delicate, expensive and can be carried out only in limited volumes.

The use of microorganisms, such as bacteria, allows production on a larger scale but has the disadvantage of leading to products which, in some cases, differ substantially from products of natural origin. Thus, the proteins which are normally glycosylated in man are not, generally, glycosylated by bacteria [P. Berman and L. A. Laskey, Trends Biochem. Sci., (1985) 10, p. 51 et seq.]. Moreover, human proteins expressed at a high level in bacteria such as E. coli often acquire an unnatural structure which is accompanied by intracellular precipitation [R. G. Schoner et al., Bio. Technol. (1985), 3, p. 151 et seq.; J. M. Schoemaker et al., EMBO J. (1985), 4, p. 775 et seq.]. Finally, for a gene to be able to be expressed in a bacterium, such as E. coli, it is essential to position an initiator codon ATG, generating a methionine before the coding sequence of the mature protein. Frequently, this residue is not excised by the methionyl aminopeptidase of E. coli [P. H. Seeburg et al., 1985, 2, p. 37 et seq.; J. M. Schoner et al., Proc. Natl. Acad. Sci. USA (1981), 81, p. 5403]. The protein obtained then has an abnormal amino acid as first residue, which may give rise to the steric inhibition of a biological activity if the start of the protein is involved in this activity. The residue may also have an immunogenic character adverse to the subsequent administration of the protein.

The use of eukaryotic microbial systems such as yeasts or mushrooms represents an interesting alternative to the use of bacterial hosts for the preparation of recombinant proteins. In fact, these organisms have all the structural and cellular organisation characteristics of more complex eukaryotic organisms, such as mammalian cells. In particular, yeasts are capable of effecting post-transcriptional and post-translational modifications important for the activity of numerous proteins. Moreover, yeasts are well known on the industrial scale: they may be cultured in high cell density, they are not pathogenic, they do not produce endotoxins and they have been used in the foodstuffs industry for a very long time.

Yeasts are already used as host organisms for the production of recombinant proteins (cf. "Yeast Genetic Engineering" Barr et al. (Eds), Butterworths, Stoneham, 1989).

In particular, yeasts of the genus Saccharomyces cerevisiae have been the subject of numerous studies (see, in particular, European Patent 60057), and the systems employing this yeast allow heterologous genes to be expressed at fairly high levels. However, the secretory capacity of S. cerevisiae constitutes a limiting factor in the exploitation of this yeast.

Other production systems have been developed with the yeasts Pichia pastoris (European Patent 402 847) or Schizosaccharomyces pombe (European Patent 385 391), and studies have also been carried out on the yeast Schwanniomyces (European Patent 394 538).

Recently, yeasts of the genus Kluyveromyces have been used as host organisms for the production of recombinant proteins. The proteins produced by this yeast are, in particular, chymosin (European Patent 96 430), thaumatin (European Patent 96 910), albumin, interleukin-1β, tPA and TIMP (European Patent 361 991) and albumin derivatives having a therapeutic function (European Patent 413 622).

However, although relatively powerful expression vectors have been developed for the use of this yeast, no studies have been carried out with the aim of improving the intrinsic performance of the cell used. In particular, there are numerous species of yeasts of the genus Kluyveromyces and, within these species, numerous different strains. The Applicant has now shown that these different strains behave in a very heterogeneous manner for the production of recombinant proteins, some of them being completely unusable.

The present invention results from the identification of a yeast strain taxonomically allied to the species Kluyveromyces lactis possessing particularly advantageous properties for the production of recombinant proteins.

The present invention thus describes the production of yeast strains modified by genetic engineering, which can be cultured in bulk and are capable of efficiently producing, and optionally of secreting into the culture medium, biologically active recombinant proteins.

One aspect of the invention therefore relates to new yeast strains for the production of recombinant proteins. More precisely, one subject of the invention relates to a host cell for the production of recombinant proteins, characterised in that the said host cell is the yeast K. lactis CBS 293.91 or a derivative or mutant thereof, containing a heterologous DNA fragment comprising a structural gene and signals permitting its expression.

In the meaning of the present invention, derivative or mutant is understood to be any strain obtained from K. lactis CBS 293.91 capable of being used for the production of recombinant proteins. In particular, such derivatives or mutants may be obtained by genetic modifications (alterations at the DNA level) or by biochemical modifications. To this end, various mutagenesis tools can be used, such as, for example, non-specific tools:

physical agents (X-rays, ultraviolet rays etc) or, chemical agents (alkylating or dialkylating agents, intercalating agents etc), or specific tools, such as the mutational insertion systems aimed at the DNA (transposons, retrotransposons, integrative plasmids, etc.).

One example of such derivatives is the strain K. lactis Y616, obtained from the strain CBS 293.91 by deletion at the level of the URA3 gene. Other mutants may be obtained by mutation at the level of genes coding for proteases, and in particular proteases conveyed by the endoplasmic reticulum, such as A and B proteases, carboxypeptidase Y, or convertases (Kex 1 in particular).

The heterologous DNA fragment may be introduced into the cell by various techniques. In general, transformation or electroporation are suitable, but it is understood that the invention is not restricted to a particular technique.

More preferentially, the heterologous DNA fragment also comprises signals permitting the secretion of the recombinant protein. These signals may correspond to the natural secretion signals of the protein under consideration, but they may also be of different origin. In particular, secretion signals derived from yeast genes may be used, such as those of the genes of the killer toxin (Stark and Boyd, EMBO J. 5 (1986) 1995) or of the alpha pheromone (Kurjan and Herskowitz, Cell 30 (1982) 933; Brake et al., Yeast 4 (1988) S436).

Still in a particular embodiment of the invention, the heterologous DNA fragment also comprises a selection marker. A marker of this type in fact enables the cells of the invention to be easily identified. The markers concerned may be, in particular, markers imparting resistance to antibiotics (such as, for example, the aph gene (Jimenez and Davies, Nature 287 (1980) 869)) or to other compounds toxic for the cell (copper ions in particular), or markers complementing the auxotrophies of the host cell (such as, for example, the URA3 gene (De Louvencourt et al., J. Bacteriol. 154 (1983) 737)).

In general, the signals permitting the expression of the structural gene are chosen from transcription promoters and terminators. It is understood that these signals are chosen depending on the structure gene and the desired result. In particular, it may be preferable in some cases to use a controllable promoter so as to be able to uncouple the growth phases of the host and that of expression of the gene. Similarly, on strength and compatibility grounds it may be preferable to use natural promoters of the structure genes in some cases and promoters of different origin in other cases.

Preferentially, the promoters used are derived from yeast genes and still more preferentially from yeast glycolytic genes. Promoters which are very particularly valuable are the promoters derived from glycolytic genes of yeasts of the genus Saccharomyces or Kluyveromyces. In particular, the promoters of genes coding for phosphoglycerate kinase (PGK), glyceraldehyde 3-phosphate dehydrogenase (GPD), enolases (ENO) or alcohol dehydrogenases (ADH) may be mentioned. Promoters derived from strongly expressed genes, such as the lactase gene (LAC4), the acid phosphatase gene (PHO5) or translation elongation factors (TEF) may also be mentioned.

Moreover, these promoter regions may be modified by mutagenesis, for example by adding supplementary transcription control elements, such as, in particular, UAS (Upstream Activating Sequence) regions. By way of example, a hybrid promoter between the promoters of the PGK and GAL1/GAL10 genes of S. cerevisiae gives good results.

In a preferred embodiment of the invention, the heterologous DNA fragment forms part of an expression plasmid, which may be autonomously replicating or integrative.

With regard to autonomously replicating vectors, these may be obtained by using autonomously replication sequences of K. lactis CBS 293.91 or its derivatives or mutants. In particular, the sequences concerned may be chromosomal sequences (ARS) originating, for example, from S. cerevisiae (Stinchcomb et al., Nature 282 (1979) 39) or from K. lactis (Das and Hollenberg, Curr. Genet. 6 (1982) 123). The vectors may also be origins of replication derived from plasmids and, for example, from the plasmid pKD1 of K. drosophilarum (European Patent 361991) or the 2 μ plasmid of S. cerevisiae (for review see Futcher, Yeast 4 (1988) 27).

With regard to integrative vectors, the latter are generally obtained using sequences homologous to certain regions of the genome of the host cell, permitting integration of the plasmid by homologous recombination.

Advantageously, according to the present invention, the structural gene codes for a protein which is pharmaceutically valuable or of value in the agri-foodstuffs industry. By way of example, the following may be mentioned: enzymes (such as, in particular, superoxide dismutase, catalase, amylases, lipases, amidases, chymosin, etc.), blood derivatives (such as serum albumin or molecular variants of the latter, alpha- or beta-globin, factor VIII, factor IX, von Willebrand's factor or fragments thereof fibronectin, 1-alpha-antitrypsin, etc.), insulin and its variants, lymphokines [such as the interleukins, interferons, colony stimulation factors (G-CSF, GM-CSF, M-CSF . . . ), TNF, TRF, MIPs, etc.], growth factors (such as growth hormone, erythropoietin, FGF, EGF, PDGF, TGF, etc.), apolipoproteins, antigenic polypeptides for the production of vaccines (hepatitis, cytomegalovirus, Epstein-Barr, herpes, etc.), vital receptors, or alternatively fusions of polypeptides, such as, in particular, fusions comprising an active part fused to a stablising part (for example fusions between albumin or albumin fragments and the receptor or part of a virus receptor (CD4, etc.)).

Preferentially, the structural gene codes for human serum albumin, a precursor of the latter or one of its molecular variants. Molecular variants of albumin are understood to be the natural variants resulting from the polymorphism of albumin, structural derivatives possessing an activity of the albumin type, truncated forms or any hybrid protein based on albumin.

Another subject of the invention relates to a process for the production of recombinant proteins, according to which process a recombinant cell as defined above is cultured and the protein produced is recovered.

As shown in the examples, this process surprisingly enables very high production levels of recombinant proteins to be obtained.

Advantageously, the process of the invention also allows the secretion of the recombinant protein into the culture medium.

The process of the invention allows the production of large amounts of recombinant proteins which are pharmaceutically valuable or of value in the agri-foodstuffs industry. It is particularly suitable for, although not restricted to, the production of human serum albumin or its molecular variants.

Further advantages of the present invention will become apparent on reading the examples which follow, which must be regarded as illustrative and non-limiting.

LEGEND TO THE FIGURES

FIG. 1: Construction of the hybrid promoter PGK/GAL. P=promoter; UAS="Upstream Activating Sequence".

Figure 2:
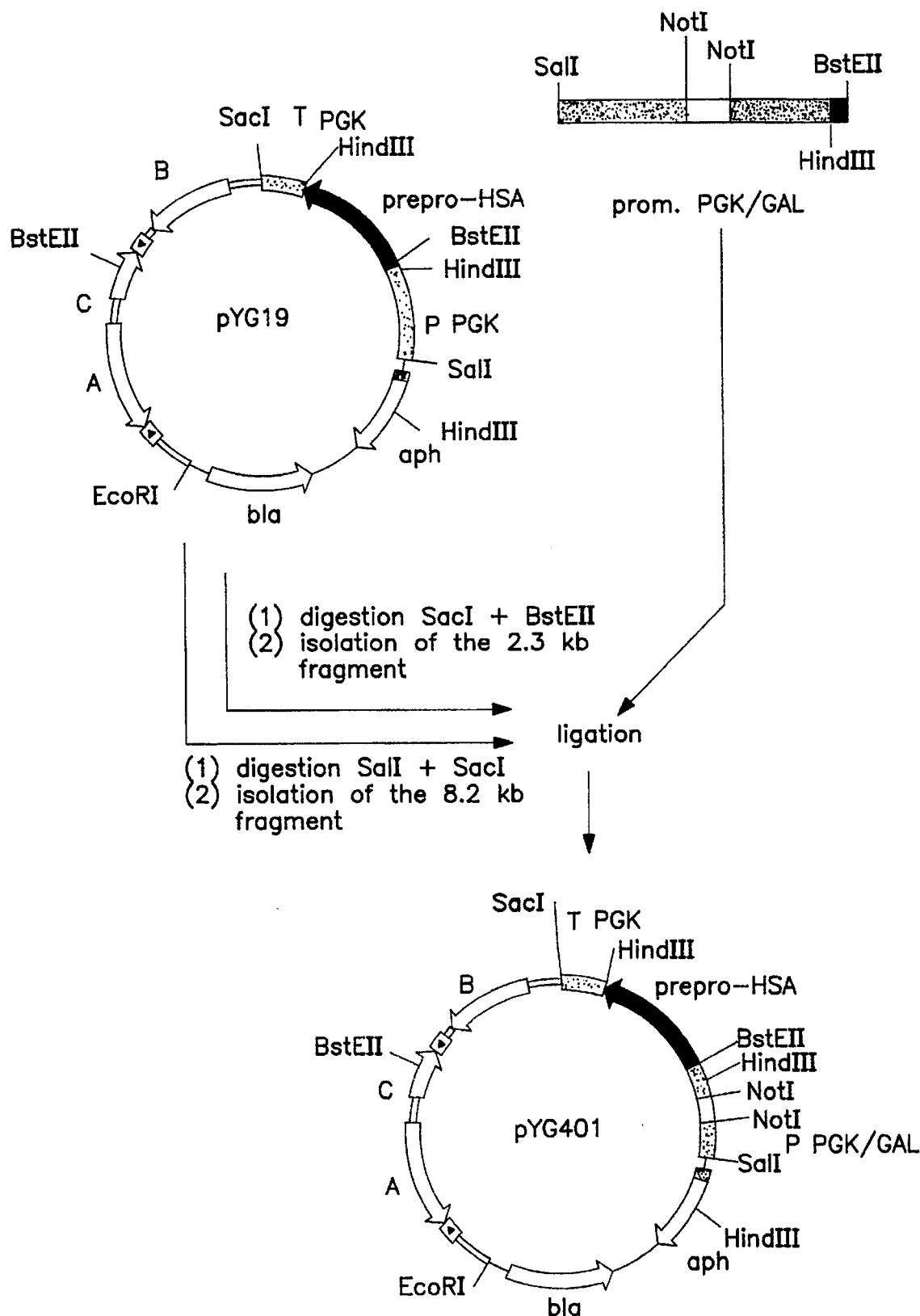

FIG. 2: Strategy for construction and representation of the vector pYG401. P=promoter; T=transcription terminator; bla=gene conferring resistance to ampicillin; aph=gene conferring resistance to geneticin (G418).

Figure 3:
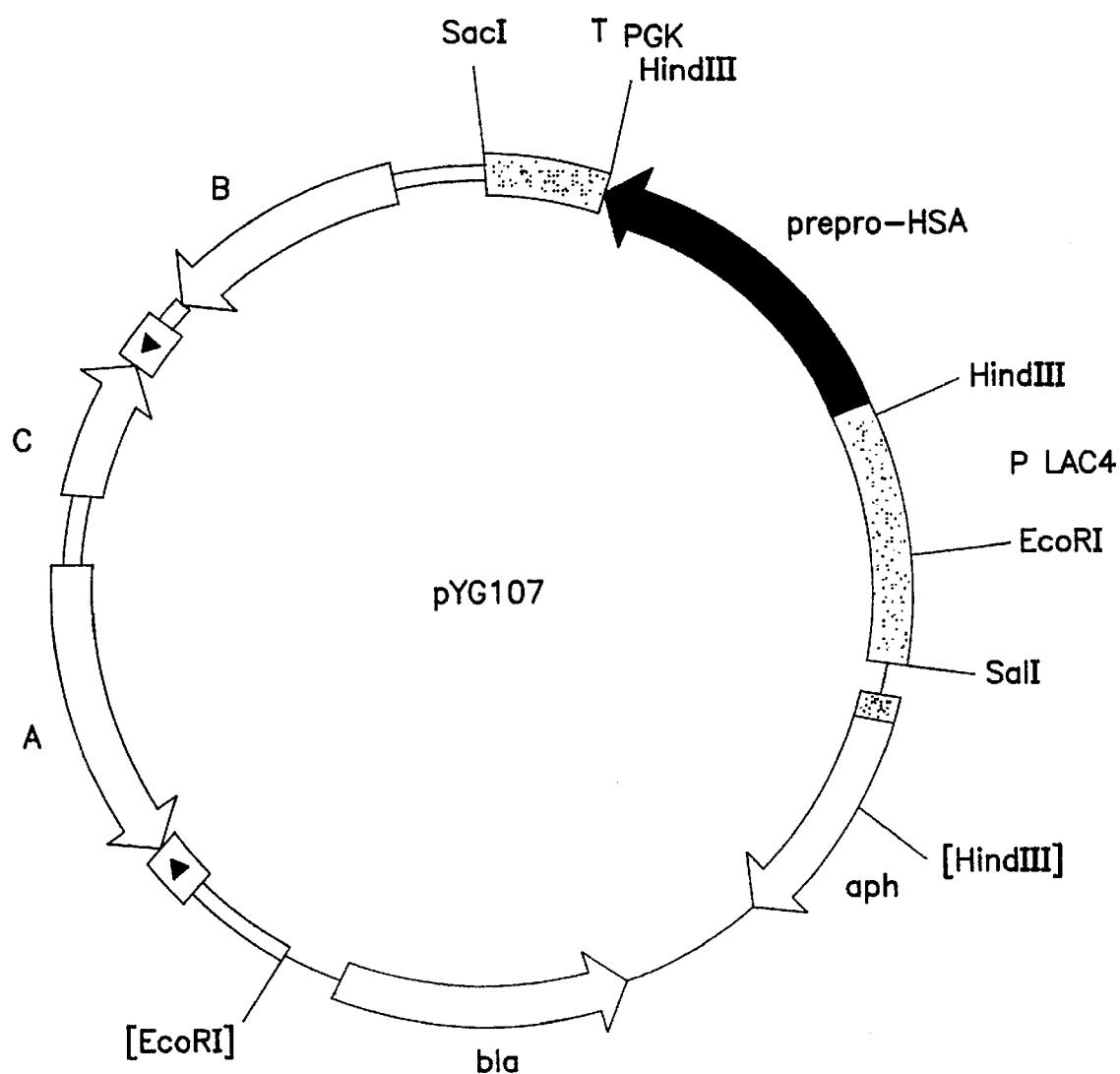

FIG. 3: Representation of the vector pYG107. The legend is identical to that for FIG. 2.

Figure 4:
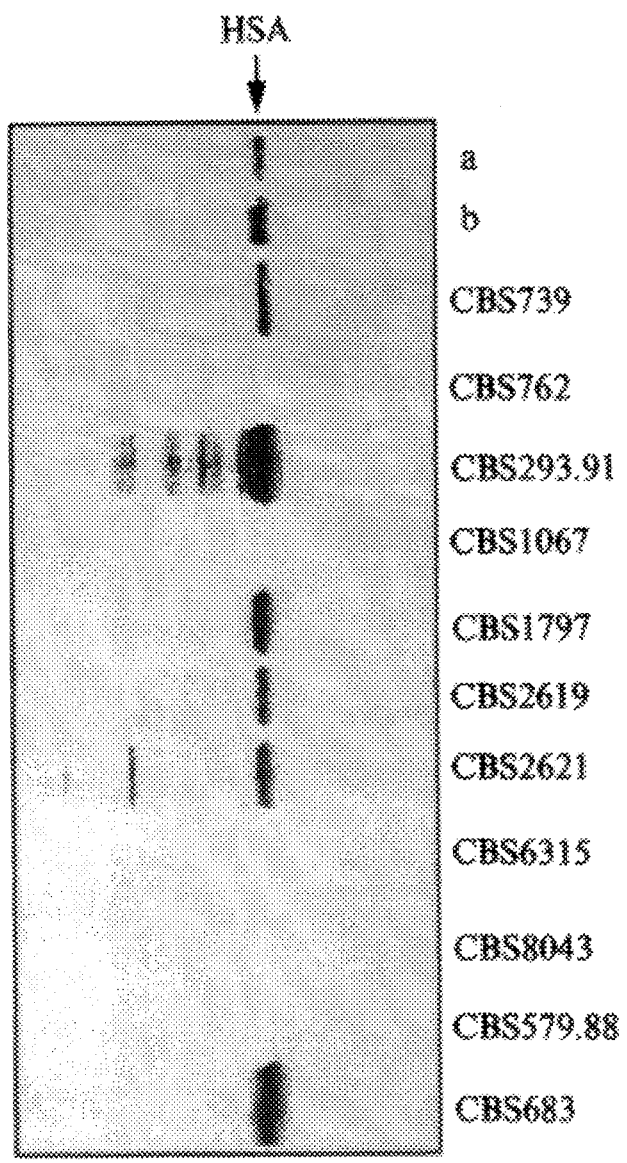

FIG. 4: Expression and secretion of albumin in various strains of K. lactis transformed by the vector pYG401. SDS-PAGE analysis (8.5 % of acrylamide), after staining with Coomassie blue, of culture supernatants (25 μl) obtained under the conditions described in the examples. Lines a and b correspond to 0.5 and 1.0 μg of standard albumin.

Figure 5:
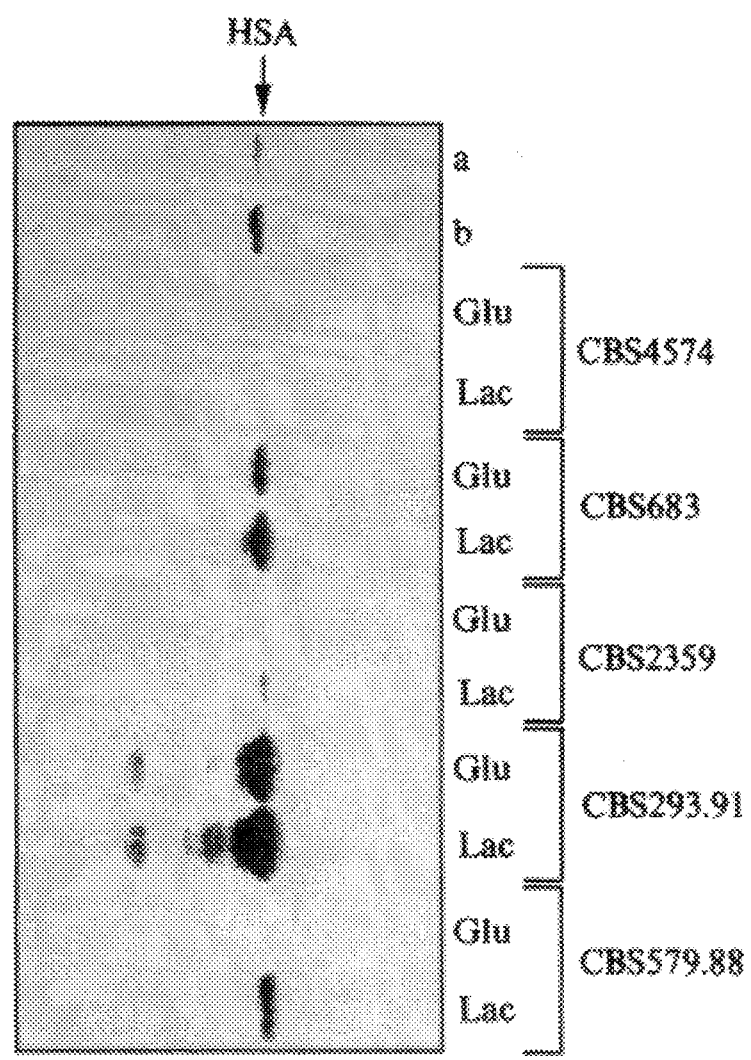

FIG. 5: Expression and secretion of albumin in various strains of K. lactis transformed by the vector pYG107. SDS-PAGE analysis (8.5 % of acrylamide), after staining with Coomassie blue, of culture supernatants (25 μl )

obtained under the conditions described in the examples. The transformed cells were cultured in M9EL10 medium (cf. example) in the presence of 2 % of glucose (Glu) or 2 % of lactose (Lac). Lines a and b correspond to 0.5 and 1.0 μg of standard albumin.

Figure 6:
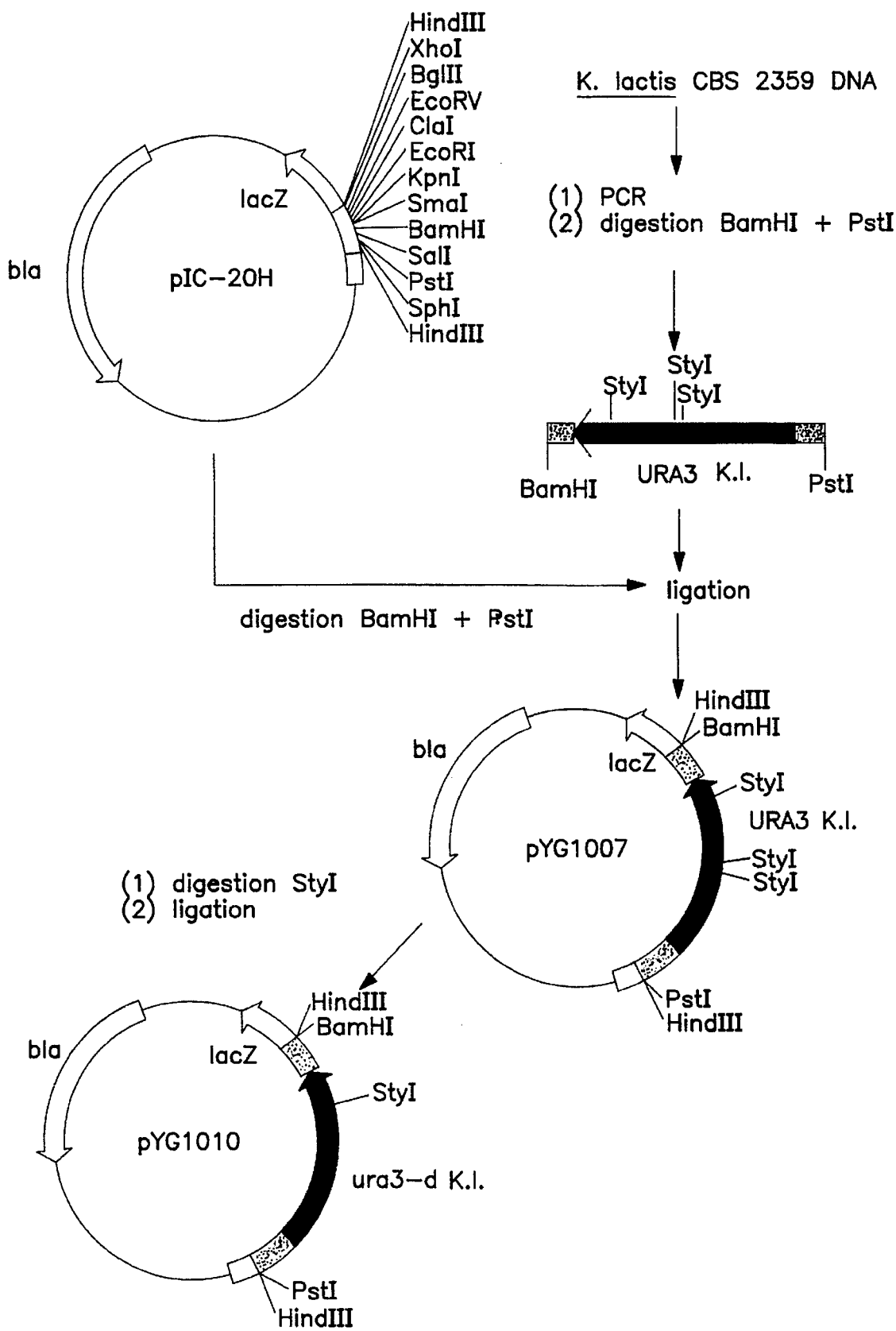

FIG. 6: Cloning strategy and modification of the URA3 gene of K. lactis CBS2359.

GENERAL CLONING TECHNIQUES

The conventional methods of molecular biology, such as plasmid DNA centrifugation using a caesium chloride/ethidium bromide gradient, digestion by restriction enzymes, gel electrophoresis, electroelution of DNA fragments from agarose gels, transformation in E. coli, etc., are described in the literature (Maniatis et al., "Molecular Cloning: a Laboratory Manual", Cold Spring Harbor Laboratory, Cold Spring Harbor, N.Y., 1986; Ausubel et al., (eds.), "Current Protocols in Molecular Biology", John Wiley & Sons, New York 1987).

Directed mutagenesis in vitro by oligodeoxynucleotides is carried out using the method developed by Taylor et al. (Nucleic Acids Res. 13 (1985) 8749–8764) using the kit supplied by Amersham. Nucleotide sequencing is effected using the dideoxy technique described by Sanger et al. (Proc. Natl. Acad. Sci. USA, 74 (1977) 5463–5467). The enzymatic amplification of specific DNA fragments is carried out by PCR ("Polymerase-catalysed Chain Reaction") under the conditions described by Mullis and Faloona (Meth. Enzym., 155 (1987) 335–350) and Saiki et al. (Science 230 (1985) 1350–1354), using a "DNA thermal cycler" (Perkin Elmer Cetus) following the manufacturer's recommendations.

EXAMPLES

Example 1

Construction of expression cassettes and/or vectors for recombinant proteins.

1.1. Construction of expression vectors for human albumin.

1.1.1. Construction of an albumin expression vector under the control of a PGK/GAL hybrid promoter.

An expression vector for human serum albumin was prepared from the plasmid pYG19 (European Patent 361 991). The latter comprises the following elements:

the plasmid pKD1 sequence, which, from pYG19, makes a plasmid having multiple copies which is stable and capable of replicating in yeasts of the genus Kluyveromyces (European Patent 361 991), an expression cassette for human serum albumin comprising the structural gene coding for the prepro form under the control of the promoter of the PGK gene of S. cerevisiae;

a bacterial replicon and a bacterial selection marker (bla gene conferring resistance to ampicillin); and the aph gene conferring resistance to G418 to yeast.

The vector pYG401 was constructed from the plasmid pYG19 by modification at the level of the expression cassette for human serum albumin. In pYG401 the albumin gene is no longer under the control of the promoter of the PGK gene of S. cerevisiae but under the control of a hybrid promoter between the promoters of the PGK and GAL1/GAL10 genes of S. cerevisiae. This hybrid promoter was obtained by replacing the UAS ("Upstream Activating Sequence") region of the PGK promoter (Stanway et al., Nucl. Acid. Res. 15 (1987) 6855) by the UAS region of the GAL1/GAL10 promoter (Johnston and Davies, Mol. Cell. Biol. 4 (1984) 1440; West et al., Mol. Cell. Biol. 4 (1984) 2467).

This hybrid promoter was constructed in the following way (cf. FIG. 1):

The production of the plasmid pYG29 has been described in detail in European Patent Application 361 991. This plasmid contains the promoter of the PGK gene of S. cerevisiae isolated from the plasmid pYG19 in the form of a SalI-HindIII fragment and cloned into the bacteriophage M13mp18. It was then modified by directed mutagenesis to introduce the following restriction sites:

1 supplementary HindIII site in position -25 with respect to the ATG. The introduction of this site makes it possible to restore, after the various cloning steps, a nucleotide sequence close to ATG identical to the natural sequence of the PGK promoter. The environment of the ATG codon is, in fact, known to have a substantial influence on the efficiency of the initiation of the translation of eukaryotic genes (Kozak, M., Microbiol. Rev. 47 (1983) 1–45; Hamilton, R., Nucl. Acid. Res 15 (1987) 3581–3593).

2 NotI sites on either side of the UAS.

The UAS of the GAL1/GAL10 promoter has been isolated from the plasmid pG1 described by Miyajima et al. (Nucl. Acid. Res 12 (1984) 6397–6414; Cloning Vectors, Pouwels et al., Elsevier (1985) VI-B-ii-2). This plasmid has been deposited with ATCC under the number 37305.

The plasmid pG1 contains a 0.8-kb fragment containing the GAL1/GAL10 promoter of S. cerevisia, inserted in the HindII site of the plasmid pUC8, from which it may be excised in the form of a BamHI-PstI fragment (FIG. 1).

This fragment was excised from pG1, purified and then digested with the enzymes RsaI and AluI, the respective cutting sites of which are located on either side of the UAS region. A 143-bp fragment was then isolated by electroelution and then brought into the form of a NotI fragment by adding a 5'-GCGGCCGC-3' linker. This fragment was then cloned in the plasmid pYG29, previously digested with NotI.

The resulting plasmid is named pYG32 (FIG. 1).

In order to obtain the expression vector carrying this hybrid promoter, the SalI-HindIII fragment carrying the hybrid promoter was isolated from pYG32 and ligated with a synthetic HindIII-BstEII adaptor composed of the following 2 complementary strands: 5'-AGC TTT ACA ACA AAT ATA AAA ACA ATG AAG TGG-3' (SEQ ID NO: 1) and 5'-GT TAC CCA CTT CAT TGT TTT TAT ATT TGT TGT AA-3' (SEQ ID NO: 2) (the codon initiating transcription is represented in bold letters). This adaptor reconstitutes the 22-bp situated immediately upstream of the PGK structural gene of S. cerevisia and contains the first codons of the gene coding for the preproHSA, up to a BstEII site present in the natural gene (FIG. 1).

The expression cassette for human albumin was then reconstituted by ligating the SalI-BstEII fragment thus obtained, carrying the hybrid promoter and the 5' end of the albumin structural gene, with the BstEII-SacI fragment isolated from the plasmid pYG19, carrying the remainder of the albumin gene and the terminator of the PGK gene of S. cerevisia (FIG. 2).

The cassette thus obtained was used to replace the SalI-SacI expression cassette carried by the plasmid pYG19.

The resulting vector is named pYG401 (FIG. 2).

1.1.2. Construction of an albumin expression vector under the control of the LAC4 promoter of K. lactis.

To test the efficiency of the inducible promoter LAC4 in the production system of the present invention, the expression vector pYG107 was constructed. This vector is identical to the pYG401 vector, in which:

(i) The EcoRI site located at the junction between the pKD1 part and the bacterial replicon is destroyed. This destruction has been obtained by cutting the pYG401 plasmid by EcoRI, filling in the cohesive ends by means of the Klenow fragment of DNA polymerase of *E. coli* and religating.

(ii) The HindIII site present in the aph gene conferring resistance to G418 is destroyed: this modification has been obtained, after sub-cloning of the aph gene into the bacteriophage M13mp7, by directed mutagenesis using the method described by Taylor et al. (Nucleic. Acid. Res. 13 (1985) 8749), using the following oligodeoxynucleotide: 5'-GAA ATG CAT AAG CTC TTG CCA TTC TCA CCG-3' SEQ ID NO: 3. This oligodeoxynucleotide converts the CTT codon coding for leucine 185 to CTC. This change does not modify the resulting protein sequence.

Modifications (i) and (ii) result in minor changes, intended solely to facilitate the subsequent cloning steps, but which do not interfere in the expression efficiency of the vectors.

(iii) The albumin expression cassette (SalI-SacI fragment) has been replaced by the SalI-SacI cassette originating from the plasmid pYG404 (European Patent 361 991), in which the gene coding for human albumin (prepro form) is under the control of the LAC4 promoter of *K. lactis*.

The structure of the vector pYG107 is shown in FIG. 3.

Example 2

Transformation of Kluyveromyces by expression vectors for recombinant proteins.

Various techniques permitting the introduction of a DNA fragment into yeast may be used.

Advantageously, the various Kluyveromyces strains used have been transformed by treating whole cells in the presence of lithium acetate and polyethylene glycol, using the technique described by Ito et al. (J. Bacteriol. 153 (1983) 163–168).

An alternative method has also been described in detail in European Patent Application 361 991.

Example 3

Expression and secretion of recombinant proteins in various yeasts of the genus Kluyveromyces.

This example demonstrates that the use of the new genetically modified yeasts of the invention makes it possible to obtain particularly high levels of production and secretion of recombinant proteins.

3.1. Human serum albumin 3.1.1. The following *Kluyveromyces lactis* strains have been transformed by the pYG401 vector, using the method described in Example 2:

*K. lactis* CBS293.91
*K. lactis* CBS739
*K. lactis* CBS762
*K. lactis* CBS1067
*K. lactis* CBS1797
*K. lactis* CBS2619
*K. lactis* CBS2621
*K. lactis* CBS6315
*K. lactis* CBS8043
*K. lactis* CBS683
*K. lactis* CBS579.88

The recombinant albumin production has been determined by the method described in European Patent Application 361 991 after a culture time of 120 hours at 28° C. with constant stirring, in YPD medium (yeast extract 10 g/l; peptone 20 g/l; glucose 20 g/l) in the presence of 2 % geneticin. The culture supernatants were obtained after centrifuging twice in succession (5 minutes at 4000 rpm and then 10 minutes at 12,000 rpm), enabling all cellular contamination to be removed. A 0.5 ml sample was then heated at 95° C. for 15 minutes in the presence of an equal volume of the following buffer: 0.125M Tris-HCl, 20% glycerol, 10% 2-mercaptoethanol, 4.6% sodium dodecyl sulphate (SDS) and 0.4% of bromophenol blue (Laemli 2×buffer, Laemli, Nature 227 (1970) 680)); and 50 µl of the solution obtained were deposited on 8.5% SDS-polyacrylamide gel. After migration, the gel was visualised using Coomassie blue.

FIG. 4 shows an increase of about 200% in the amount of albumin produced in the system of the invention, compared with the best systems previously described (European Patent 361 991).

3.1.2. The following *Kluyveromyces lactis* strains were transformed by the pYG107 vector, using the method described in Example 2:

*K. lactis* CBS4574
*K. lactis* CBS683
*K. lactis* CBS2359
*K. lactis* CBS293.91
*K. lactis* CBS579.88

The recombinant albumin production was determined using the method described in European Patent Application 361 991 and in Example 3.1.1. after a culture time of 120 hours at 28° C. with constant stirring, in M9EL10 medium in the presence of 20 g/l glucose or 20 g/l lactose. The M9EL10 medium consists of M9 medium (Maniatis et al., mentioned above) supplemented by 10 g/l of yeast extract.

FIG. 5 shows that the amount of albumin produced is always higher in the system of the invention. It also shows that the production is 2 to 3 times better in a medium containing lactose (LAC4 promoter inducer) than in a glucose medium. Moreover, it finally shows that, surprisingly, the strain CBS293.91 is semi-constitutive for the production of recombinant proteins under the control of the LAC4 promoter.

3.2. Interleukin-1 β

The following *Kluyveromyces lactis* strains have been transformed by the pSPHO-IL35 vector (cf. European Patent 361 991) using the method described in Example 2:

*K. lactis* CBS683
*K. lactis* CBS293.91
*K. lactis* CBS579.88

Example 4

Construction of a ura3 mutant of *K. lactis* CBS293.91.

A ura3 derivative has been prepared from *K. lactis* CBS293.91. Such a derivative retains the properties of the initial strain, with, in addition, an auxotrophy for uracil, which may be used as selection marker. In order to prevent the occurrence of any reversion, this mutant was prepared by deletion of part of the chromosomal URA3 allele of CBS293.91. This mutagenesis technique also makes it possible to avoid the use of non-specific mutagenic agents capable of modifying other genomic regions of the cell.

4.1. Cloning and modification of the URA3 gene of *K. lactis* CBS2359 (FIG. 6).

The URA3 gene of *K. lactis* coding for orotidine-5-phosphate decarboxylase (Shuster et al., Nucl. Acid. Res. 15 (1987) 8573) has been cloned in the form of a 1.2-kb BamHI-PstI fragment using the PCR technique (cf. general cloning techniques), from a genomic DNA extract (Rose et al., "Methods in Yeast Genetics" Cold Spring Harbor Laboratory Press, N.Y., 1990) from *K. lactis* CBS2359 using the following oligodeoxynucleotides:

5'-GGAAGCTTGGCTGCAGGAATTGTCGTTCATG GTGACAC-3' and (SEQ ID NO.: 4)

5'-CCGAATTCCCGGATCCCATAATGAAAGAGAG AGAGAAGCAAAC-3' (SEQ ID NO. 5).

The fragment obtained was then sub-cloned in the BamHI and PstI sites of the pIC-20H plasmid (Marsh et al., Gene 32 (1984) 481) to give the plasmid pYG1007 (FIG. 6). This fragment was then modified by deletion of an internal fragment of the URA3 gene comprising 286 bp, located between the StyI sites, followed by religation in the presence of ligase. This new plasmid is named pYG1010 (FIG. 6).

4.2 Transformation of *K. lactis* CBS293.91 by the deleted URA3 9 gene.

The CBS293.91 strain was transformed by 10 µg of the PstI-BamHI fragment isolated from the plasmid pYG1010 by electroelution and containing the deleted URA3 gene. After a sudden rise in temperature to 42° C. ("heat shock") and 2 successive washings with water, 600 µl of YPD medium were added and the cells were incubated overnight. The cells were then plated out on synthetic minimal SD medium ("Bacto-yeast nitrogen base" without amino acids (Difco) 6.7 g; glucose 20 g; Bacto-agar 20 g, distilled water 1,000 ml) in the presence of uracil (100 µg/ml), uridine (100 µg/ml) 15 mM 5-fluoroorotate (5FO).

Clones appeared at the end of 4 to 5 days. They were subcultured on YPD medium so as to obtain isolated colonies.

From the first subculture, 3 clones resulting from the colony which initially appeared on SD+5FO medium were reisolated on YPD medium (secondary subculture).

The clones resulting from the secondary subculture were then tested for the Ura3$^-$ phenotype using the drop test on SD and SD+uracil medium (Jund and Lacroute, J. of Bact. 102 (1970) 607–615; Bach and Lacroute, Mol. Gen. Genet. 115 (1972) 126–130). The ura3 genotype of the clones thus obtained was checked by:

PCR reaction using the oligodeoxynucleotides described for cloning under 4.1., which allows identification of the clones carrying only the deleted URA3 gene;

complementation using the pKan707 plasmid (European Patent 361 991) carrying the intact URA3 gene of *S. cerevisia*, known for its ability to complement the ura3 auxotroph in *K. lactis* (De Louvencourt, mentioned above); and Southern blotting on genomic DNA of the identified clones, using, as probe, the URA3 gene of *K. lactis* isolated in Example 4.1., labelled with $^{32}$p using the technique described by Feinberg and Vogelstein (Anal. Biochem. 132 (1983) 6).

The selected ura3 mutant is named *K. lactis* Y616.

A sample of the strain *K. lactis* Y616 was deposited on 11 Jun. 1991 with the Centraalbureau voor Schimmelkulturen (CBS) in Baarn in the Netherlands under the conditions of the Budapest Treaty, under number CBS294.91. The strain *K. lactis* CBS293.91 corresponds to the strain CBS1065 refiled on 11 Jun. 1991 under the conditions of the Budapest Treaty.

---

We claim:

1. Host cell for the production of recombinant proteins, characterised in that the said host cell is the yeast *K. lactis* CBS293.91 or a derivative or mutant thereof which produces substantially equivalent levels of recombinant proteins, containing a heterologous DNA fragment comprising a structural gene and signals permitting its expression.

2. The host cell according to claim 1, wherein said heterologous DNA fragment also comprises signals permitting the secretion of the recombinant protein.

3. The host cell according to claim 1, wherein said heterologous DNA fragment also comprises a selectable marker.

4. The host cell according to claim 1, wherein said signals permitting expression of the structural gene are selected from the group consisting of transcriptional promoters and terminators.

5. The host cell according to claim 4, wherein said transcriptional promoters are promoters of yeast genes.

6. The host cell according to claim 1 wherein said heterologous DNA fragment forms part of an autonomously replicating or integrative expression plasmid.

7. The host cell according to claim 6, wherein said heterologous DNA fragment forms part of an autonomously replicating expression plasmid, comprising chromosomal sequences of ARS type or a replication origin derived from the pKD1 plasmid of *K. drosophilarum* or the 2 μ plasmid of *S. cerevisiae*.

8. The host cell according to claim 1, wherein said protein is selected from the group consisting of enzymes wherein said enzymes are selected from the group consisting of superoxide dismutase, catalase, amylases, lipases, amidases, and chymosin, blood derivatives wherein said blood derivatives are selected from the group consisting of serum albumin or molecular variants of the latter, alpha- or beta-globin, factor VIII, factor IX, von Willebrand's factor (vWF) or biologically active fragments of said vWF, fibronectin, and 1-alpha-antitrypsin, insulin and its variants, lymphokines wherein said lymphokines are selected from the group consisting of the interleukins, interferons, colony stimulation factors selected from the group consisting of G-CSF, GM-CSF, and M-CSF, TNF, TRF, and MIPs, growth factors wherein said growth factors are selected from the group consisting of growth hormone, erythropoietin, FGF, EGF, PDGF, and TGF, apolipoproteins, antigenic polypeptides for the production of vaccines wherein said polypeptides are selected from the group consisting of hepatitis, cytomegalovirus, Epstein-Barr, and herpes, viral receptors, and fusion polypeptides comprising an active part fused to a stabilising part.

9. The host according to claim 8, wherein said protein is chosen from human serum albumin and its molecular variants.

10. A process for the production of recombinant proteins, wherein a cell according to claim 1 cultured and the protein produced is recovered.

11. The process according to claim 10, wherein said protein is secreted into the culture medium.

12. The process according to claim 10, wherein said protein is selected from the group consisting of enzymes wherein said enzymes are selected from the group consisting of superoxide dismutase, catalase, amylases, lipases, amidases, and chymosin, blood derivatives wherein said blood derivatives are selected from the group consisting of serum albumin or molecular variants of the latter, alpha- or beta-globin, factor VIII, factor IX, von Willebrand's factor (vWF) or biologically active fragments of said vWF, fibronectin, and 1-alpha-antitrypsin, insulin and its variants, lymphokines wherein said lymphokines are selected from the group consisting of the interleukins, interferons, colony stimulation factors selected from the group consisting of G-CSF, GM-CSF, and M-CSF, TNF, TRF, and MIPs, growth factors wherein said growth factors are selected from the group consisting of growth hormone, erythropoietin, FGF, EGF, PDGF, and TGF, apolipoproteins, antigenic polypeptides for the production of vaccines wherein said polypeptides are selected from the group consisting of hepatitis, cytomegalovirus, Epstein-Barr, and herpes, viral receptors, and fusion polypeptides comprising an active part fused to a stabilising part.

13. The process according to claim 12, wherein said protein is chosen from human serum albumin and its molecular variants.

14. The yeast *K. lactis* Y616 No. CBS294.91.

15. The process according to claim 11, wherein said protein is selected from the group consisting of enzymes wherein said enzymes are selected from the group consisting of superoxide dismutase, catalase, amylases, lipases, amidases, and chymosin, blood derivatives wherein said blood derivatives are selected from the group consisting of serum albumin or molecular variants of the latter, alpha- or beta-globin, factor VIII, factor IX, von Willebrand's factor (vWF) or biologically active fragments of said vWF, fibronectin, and 1-alpha-antitrypsin, insulin and its variants, lymphokines wherein said lymphokines are selected from the group consisting of the interleukins, interferons, colony stimulation factors selected from the group consisting of G-CSF, GM-CSF, and M-CSF, TNF, TRF, and MIPs, growth factors wherein said growth factors are selected from the group consisting of growth hormone, erythropoietin, FGF, EGF, PDGF, and TGF, apolipoproteins, antigenic polypeptides for the production of vaccines wherein said polypeptides are selected from the group consisting of hepatitis, cytomegalovirus, Epstein-Barr, and herpes, viral receptors, and fusion polypeptides comprising an active part fused to a stabilising part.

16. The host cell according to claim 5 wherein said promoters are promoters of yeast glycolytic genes.

17. The host cell according to claim 5 wherein said promoters are promoters of strongly expressed yeast genes.

18. The host cell of claim 1, characterised in that said host cell is the yeast *K. lactis* Y616, deposited as CBS294.91, containing a heterologous DNA fragment comprising a structural gene and signals permitting its expression.

19. A process for the production of recombinant proteins, wherein a cell according to claim 18 is cultured and the protein produced is recovered.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:1:

AGCTTTACAA CAAATATAAA AACAATGAAG TGG    3 3

( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

GTTACCCACT TCATTGTTTT TATATTTGTT GTAA    3 4

(2) INFORMATION FOR SEQ ID NO:3:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:3:

GAAATGCATA AGCTCTTGCC ATTCTCACCG 30

(2) INFORMATION FOR SEQ ID NO:4:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:4:

GGAAGCTTGG CTGCAGGAAT TGTCGTTCAT GGTGACAC 38

(2) INFORMATION FOR SEQ ID NO:5:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: other nucleic acid (xi) SEQUENCE DESCRIPTION: SEQ ID NO:5:

CCGAATTCCC GGATCCCATA ATGAAAGAGA GAGAGAGAAG CAAAC 45